(12) United States Patent
Roby et al.

(10) Patent No.: US 6,890,345 B2
(45) Date of Patent: May 10, 2005

(54) PRETREATMENT FOR LUBRICATED SURGICAL NEEDLES

(75) Inventors: Mark S. Roby, Killingworth, CT (US); John Kennedy, Guilford, CT (US); Nicholas Maiorino, Branford, CT (US); Alan Cabezas, Ansonia, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 167 days.

(21) Appl. No.: 09/964,902

(22) Filed: Sep. 27, 2001

(65) Prior Publication Data
US 2003/0114883 A1 Jun. 19, 2003

(51) Int. Cl.$^7$ .............................................. A61B 17/04
(52) U.S. Cl. ..................................... 606/222; 606/223
(58) Field of Search ............................... 606/222–227; 604/264, 265

(56) References Cited

U.S. PATENT DOCUMENTS

| | | | |
|---|---|---|---|
| 3,574,673 A | 4/1971 | Schweiger | 117/132 |
| 3,767,385 A | 10/1973 | Slaney | 75/122 |
| 3,816,920 A | 6/1974 | Sastri | 30/346.54 |
| 4,448,847 A | 5/1984 | Bell et al. | 428/413 |
| 4,647,479 A | 3/1987 | Montes | 427/327 |
| 4,959,068 A * | 9/1990 | Bendel et al. | 606/222 |
| 5,181,416 A | 1/1993 | Evans | 73/104 |
| 5,186,972 A * | 2/1993 | Williams et al. | 427/2.28 |
| 5,258,013 A | 11/1993 | Granger et al. | 606/223 |
| 5,266,359 A * | 11/1993 | Spielvogel | 427/388.4 |
| 5,342,901 A | 8/1994 | Kogure et al. | 525/330.5 |
| 5,458,616 A * | 10/1995 | Granger et al. | 606/223 |
| 5,523,161 A | 6/1996 | Goodwin | 428/421 |
| 5,536,582 A * | 7/1996 | Prasad et al. | 428/450 |
| 5,607,663 A | 3/1997 | Rozzi et al. | 424/49 |
| 5,707,740 A | 1/1998 | Goodwin | 428/410 |
| 5,869,141 A | 2/1999 | Blohowiak et al. | 427/309 |
| 5,876,208 A | 3/1999 | Mitra et al. | 433/217 |
| 5,928,268 A * | 7/1999 | Butwell et al. | 606/222 |
| 5,958,578 A | 9/1999 | Blohowiak et al. | 428/336 |
| 5,980,990 A | 11/1999 | Goodwin | 427/309 |
| 6,015,398 A * | 1/2000 | Arimatsu et al. | 604/272 |
| 6,025,025 A | 2/2000 | Bartrug et al. | 427/302 |
| 6,143,420 A | 11/2000 | Heimann et al. | 428/453 |
| 6,165,257 A | 12/2000 | Heimann et al. | 106/14.21 |

* cited by examiner

Primary Examiner—Gary Jackson

(57) ABSTRACT

A method for siliconizing surgical needles is provided whereby the needles are treated with acid before they are siliconized.

4 Claims, 1 Drawing Sheet

PRETREATMENT FOR LUBRICATED SURGICAL NEEDLES

BACKGROUND

1. Technical Field

Figure 1:
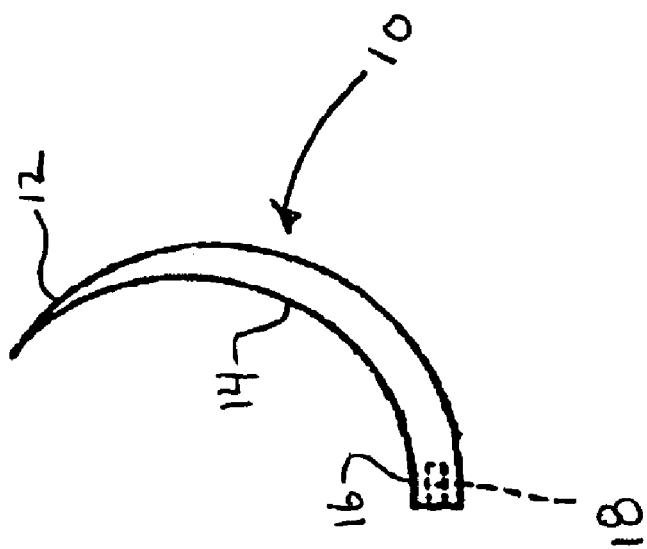

The present disclosure generally relates to a method for improving the adhesion of lubricants to surgical needles. More particularly, the present disclosure is directed to a method for siliconizing surgical needles in which the needles are treated with an acid solution before a siliconizing material is applied to the needles. The present disclosure also relates to needles made by this process having reduced tissue penetration force.

2. Background of Related Art

The siliconization of metallic cutting edges of articles such as, for example, razor blades, hypodermic needles, surgical needles, scissors, scalpels, and curettes, is known. For example, a process is known for preparing a siliconized surgical needle in which an amino alkyl siloxane is applied to the surface of the needle by immersion in a solution or by spraying and then cured at elevated temperature in order to produce a silicone coating. A product sold by Dow Coming under the name "MDX4-4159" can be used as the amino alkyl siloxane, with the heat treatment being carried out for half an hour or longer at about 120° C.

U.S. Pat. No. 3,574,673, the contents of which are incorporated by reference herein, discloses the silicone coating of a cutting edge employing a siliconization fluid containing a mixture of copolymerizable silicones made up of an aminoalkyl siloxane, specifically a (polyaminoalkyl) alkoxysilane, and a dimethylpolysiloxane.

In order to reduce the force of penetration, it is also known to immerse surgical needles in a solution of a condensable polymethyl siloxane in a mixture of n-heptane and xylene and then to remove the solvent by thermal after-treatment for one hour at 100° C. The product sold by Dow Corning under the name "Syl-Off DC 23", which exhibits an average degree of polymerization of about 8000, is suitable as the condensable polymethyl siloxane.

Other examples include U.S. Pat. Nos. 5,258,013 and 5,458,616 which disclose coating surgical needles with a siliconization material containing an aminoalkyl siloxane and a cyclosiloxane employing ultrasonic radiation. The siliconization material can be applied in a solvent carrier, e.g., hexane or heptane.

The previously known processes produce surgical needles in which the force of penetration is clearly reduced compared with untreated needles. It would be advantageous to provide siliconized surgical needles which exhibit an even greater reduction in penetration force upon repeated passages through tissue during a suturing operation.

SUMMARY

It has been discovered that pretreating a surgical needle with acid prior to the application of a silicone coating provides a siliconized surgical needle in which the needle exhibits an average tissue penetration force below that of a standard siliconized surgical needle. A siliconized needle in accordance with this disclosure can be obtained by applying a pretreating solution containing an acid to the surface of a needle to be coated, and then applying a lubricant composition.

The expression "standard siliconized surgical needle" or "standard needle" as used herein refers to a commercially available siliconized surgical needle, e.g., the siliconized surgical needles attached to sutures marketed by Ethicon, Inc. (Somerville, N.J.).

The acid of the acid solution can be an inorganic acid (such as, for example hydrochloric acid, sulfuric acid, phosphoric acid, hydrobromic acid and/or nitric acid), or an organic acid (such as, for example, citric acid, acetic acid, tartaric acid and/or trifluoroacetic acid).

After treatment with an acid, the needles are coated with a lubricant composition. In one embodiment, the lubricant composition includes an aminoalkyl siloxane and at least one other siloxane such as a cyclosiloxane which is copolymerizable therewith. In another embodiment, the lubricant composition is a mixture that includes at least one polydialkylsiloxane having a molecular weight sufficient to provide a viscosity of the mixture of at least about 10,000 cp and at least one other siliconization material. In yet another embodiment, the lubricant composition includes a polydialkylsiloxane and at least one siliconization material which does not covalently bond with the polydialkylsiloxane.

While the amount of force required to achieve penetration of tissue during suturing may initially be about the same for the siliconized surgical needle of this disclosure and a presently available siliconized surgical needle, and while both needles will tend to experience an increase in penetration force with each successive passage through tissue, at the conclusion of any given number of such passages, the siliconized needle of this disclosure will exhibit significantly less penetration force than the presently available needle. Thus, the siliconized needle of this disclosure will advantageously retain its initial tissue penetration characteristics to a greater extent than a presently available siliconized needle in a manner which is particularly advantageous, as it reduces the effort required in the suturing operation.

DESCRIPTION OF THE PREFERRED EMBODIMENTS

Preferred embodiments of the present disclosure involve pretreating surgical needles with an acid solution prior to coating them with a siliconization material to produce siliconized surgical needles. It has been discovered that by pretreating a surgical needle with a pretreating solution containing an acid and then coating the needle with a silicone-containing lubricant composition, a siliconized surgical needle is provided which exhibits a significantly reduced tissue penetrating force after a number of passages through tissue. Thus, the average tissue penetration force of the siliconized needle herein will advantageously be less than about 10%, preferably less than about 20% and more preferably less than about 30%, of the average tissue penetration force of a commercially available siliconized needle presently on the market from after about 5 to about 20 passes through tissue.

As seen in FIG. 1, a surgical needle 10 generally includes a tip portion 12, a body portion 14 and a needle attachment portion 16. The coatings described herein can be applied to needles of any configuration. Thus the needle may be curved, straight or have a compound configuration. The cross section of the needle can be round, oval, triangular, rectangular, or any other geometry. The needle may include cutting edges. The tip portion may be pointed or blunt. The suture attachment portion can be, e.g., an eye, a slot or, as shown in FIG. 1, a bore 18.

Surgical needles which can be treated and coated in accordance with this disclosure can be manufactured from a variety of metals. Such metals include, but are not limited to, Series 400 and Series 300 stainless steels, and the quaternary alloys disclosed in U.S. Pat. Nos. 3,767,385 and 3,816,920, the contents of which are incorporated by reference herein. A preferred quaternary alloy possesses the ranges of components set forth below in Table I:

TABLE I

COMPOSITION OF SURGICAL NEEDLE QUATERNARY ALLOY (WT. %)

| Component(s) | Broad Range | Preferred Range | Most Preferred Range |
| --- | --- | --- | --- |
| Nickel | 10–50 | 24–45 | 30–40 |
| Cobalt | 10–50 | 25–45 | 30–40 |
| Nickel + Cobalt | 50–85 | 60–80 | 65–75 |
| Chromium | 10–30 | 12–24 | 15–22 |
| Molybdenum, tungsten and/or niobium (columbium) | 5–20 | 8–16 | 10–13 |

Another preferred quaternary alloy within Table I which can be utilized for the siliconized needle of this disclosure, designated MP35N, is available in wire form from Maryland Specialty Wire, Inc. (Cockeysville, Md.) and contains (nominal analysis by weight): nickel, 35%; cobalt, 35%; chromium, 20% and molybdenum, 10%.

In general, applying a pretreating solution containing an acid to the surface of a surgical needle followed by applying a silicone coating mixture will provide a siliconized surgical needle meeting the requirements of this disclosure.

To enhance formation of the silicone coating and its adherence to a surgical needle, the metal surface of the needle is pretreated with a solution containing an acid. Metal surfaces normally tend to be covered with a heterogeneous layer of oxides and other impurities. This covering can hinder the effectiveness of the silicone coating formation. Thus, it becomes useful to convert the needle surface to a homogenous state thereby permitting more complete and uniform silicone coating formation. Surface preparation can be accomplished using a pretreatment solution, either an acid bath or spray, to dissolve the oxide layers as well as wash away impurities. The use of organic solvents and detergents or surfactants can also aid in this surface preparation process.

The pretreating solutions of the present disclosure contain acids that are selected for their ability to enhance the adhesion of siliconization material(s) to the surface of a surgical needle in order to form a silicone coating. Suitable acid solutions include solutions of mineral acids such as, for example, hydrochloric acid, sulfuric acid, phosphoric acid, hydrobromic acid and nitric acid. Organic acids such as, for example, carboxylic acids, are also useful. Preferable carboxylic acids include citric acid, acetic acid, tartaric acid and trifluoroacetic acid. In a particularly useful embodiment, citric acid is used as the acid in the pretreating solution.

Where organic acid solutions are selected, strong acid solutions are preferred, with solutions having a pH of less than 7 and more preferably less than 4.5. The pretreating solution is preferably an aqueous solution from about 10 to about 100 g/L of one or more water soluble carboxylic acids or water soluble salts of these acids.

Where the acid in the pretreating solution is citric acid, the citric acid, or salt thereof, is dissolved in deionized water so that the acid concentration is about 1.0 to about 10 wt. % carboxylic acid. As can be appreciated by one of skill in the art, lower or higher acid concentrations may be used with correspondingly more or less time on the needle to improve the adherence of the silicone coating on the needles' surface.

The acid solution may be applied to the substrate by any conventional technique such as dipping, flowing, spraying and, preferably, wiping.

Where the acid solution is volatile and will evaporate from the needle without leaving a residue, the acid is applied to the needle and allowed to evaporate, whereupon siliconization material is applied to the needle. Volatile acid solutions are defined herein as those which are capable of volatilizing at ambient conditions within a short time period (i.e., within about 10 minutes or less) after application to the needle. Examples of volatile acid solutions include hydrochloric, hydrobromic, acetic, nitric, and trifluoroacetic acid solutions.

Where the acid solution is non-volatile, or is volatile but leaves behind a residue upon evaporation, the needle should be rinsed after the acid pretreatment to remove the acid solution or its residue. Non-volatile acid solutions are defined herein as those which are not capable of volatilizing at ambient conditions within a short time period (i.e. within about 10 minutes or less) after application to the needle. Examples of non-volatile acids include sulfuric, tartaric, citric, and phosphoric acids. The rinsing solutions may include water or alcohol, with water being preferred. After rinsing, the needle is dried and the siliconization material applied to the needle.

It is believed that the acid solution enhances the adherence of the siliconization material to form the silicone coating by removing contaminating residues from the surface of the needle and increasing the number of bonding sites on the surface of the needle available for reaction with the siliconization material.

The temperature of the pretreating solution is desirably in the range of from about 20 to about 95° C. The pretreating time can be in the range of about 2 to about 90 minutes. In one embodiment of the present disclosure, the needles are dipped into a bath containing the pretreating solution. It is preferred to place the needles onto a wire screen mesh, immerse the needles into the pretreating solution, and then remove them from the pretreating solution. The needles are rinsed with hot water and then allowed to dry and placed onto another wire screen mesh for exposure to a lubricant composition.

Once the surface is pretreated, the surface can then be subjected to further activation, if necessary, to enhance the formation and adherence of the lubricant composition, including but not limited to oxidation by any suitable method. Examples of suitable methods for application of oxidizers include immersion in hydrogen peroxide, sodium peroxide, potassium permanganate and mixtures thereof.

A lubricant composition is applied to at least the tip portion of the needle. In particularly useful embodiments, the entire needle receives the lubricant composition. Where the lubricant composition is curable, it may be necessary to avoid filling or blocking any eye, slit or bore present at the suture attachment portion of the needle.

The lubricant composition includes at least one silicone material. As used herein, the term silicone means silicones and derivatives of silicone chemistry, including but not limited to silicone fluids, silicone oils, silicone-organic copolymers, silicone resins, volatile silicones (cyclomethicones), linear silicones, cyclosiloxanes, polydialkylsiloxanes, polydimethylsiloxanes, dimethicone copolyols, silicone glycols, aminofunctional silicones, polymeric silicones, silicone waxes, such as high molecular weight dimethicones, and silicone derivative waxes.

In one embodiment, the lubricant composition is Dow Corning® MDX 4-4159 Fluid ("MDX Fluid"), a 50 percent active solution of dimethyl cyclosiloxanes and dimethoxysilyldimethylaminoethylaminopropyl silicone polymer in a mixture of Stoddard solvent (mineral spirits) and isopropyl alcohol. It is preferred to apply the MDX Fluid to a surface of the pretreated surgical needle by dipping, wiping, spraying, etc. in the form of a first dilute organic solution, e.g., prepared with a solvent such as, for example, a hydrocarbon solvent possessing from about 5 to about 10 carbon atoms, e.g., pentane, hexane, heptane, octane, etc., trichlorotrifluoroethane, 1,1,1-trichloroethane, mineral spirits, alcohols, e.g., isoopropyl alcohol, and the like and mixtures thereof. It is preferred to dilute MDX Fluid (or other siliconization material) with hexane and isopropyl alcohol with MDX Fluid being present in the concentration range of from about 10 g/l to about 80 g/l and preferably from about 20 g/l to about 40 g/l.

In a particularly useful embodiment, the lubricant composition is a mixture containing at least a polydialkylsiloxane having a molecular weight sufficient to provide a viscosity of the coating mixture of at least about 10,000 cp and at least one siliconization material followed by curing.

Suitable polydialkylsiloxanes for use in forming the coating mixture herein include polydimethylsiloxanes, polydiethylsiloxanes, polydipropylsiloxanes, polydibutylsiloxanes and the like with polydimethylsiloxanes being preferred. Particularly preferred polydimethylsiloxanes are polydimethylsiloxanes having a molecular weight sufficient to provide a viscosity of the coating mixture of at least about 10,000 cp and preferably of at least about 30,000 cp. Such polydimethylsiloxanes for use herein are the products sold by Dow Corning under the name "Syl-Off DC 23", which is suitable as a high density condensable polydimethylsiloxane, and NuSil Technology under the name "MED1-4162" (30,000 cp).

Suitable siliconization materials for addition with the foregoing polydialkylsiloxanes to form the coating mixtures of this disclosure include siliconization materials containing an aminoalkyl siloxane and at least one other copolymerizable siloxane, e.g., an alkylpolysiloxane or a cyclosiloxane; a silicone oil, e.g., one sold by Dow Corning Corporation under the name Dow 36 Medical Fluid (350 to 12,500 centistokes), and the like with the siliconization material containing an aminoalkyl siloxane and at least one other copolymerizable siloxane being preferred. Generally, the preferred siliconization material includes (a) from about 5 to about 70 weight percent of an aminoalkyl siloxane of the general formula

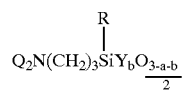

wherein R is a lower alkyl radical containing no more than about 6 carbon atoms; Y is selected from the group consisting of —OH and —OR' radicals in which R' is an alkyl radical of no more than about 3 carbon atoms; Q is selected from the group consisting of hydrogen, —CH$_3$ and —CH$_2$CH$_2$NH$_2$; a has a value of 0 or 1, b has a value of 0 or 1 and the sum of a+b has a value of 0, 1 or 2; and (b) from about 30 to about 95 weight percent of a methyl substituted siloxane of the general formula

wherein R" is selected from the group consisting of —OH and —CH$_3$ radicals and c has a value of 1 or 2. The two components of this siliconization material copolymerize, forming a lubricating coating on the surface of the needle.

In addition to, or in lieu of, the foregoing second copolymerizable siloxane, one can use one or more cyclosiloxanes such as, e.g., those described in the "Encyclopedia of Polymer Science and Engineering", Mark et al., eds., 2$^{nd}$ ed., Vol. 15, John Wiley & Son (1989), p. 207 et seq., the contents of which are incorporated by reference herein, provided, of course, the total amount of the second copolymerizable siloxane(s) is within the aforestated range.

A particularly preferred siliconization material for use herein in combination with the aforementioned polydimethylsiloxane(s) to form the coating mixture is MDX Fluid, which, as noted above, is an active solution of dimethyl cyclosiloxanes and dimethoxysilyldimethylaminoethylaminopropyl silicone polymer in a mixture of Stoddard solvent (mineral spirits) and isopropyl alcohol. Another preferred siliconization material is NuSil Technology's MED-4159.

In one embodiment of the present disclosure, the coating mixture can be formed by adding a first solution of at least one of the foregoing polydialkylsiloxanes in a solvent with a second solution of at least one of the foregoing siliconization materials in a solvent. Under preferred conditions, the first solution can be prepared by adding Syl-Off DC 23, MED1-4162 or both in a solvent such as, for example, a hydrocarbon solvent having from about 5 to about 10 carbon atoms, e.g., pentane, hexane, heptane, octane, etc., xylene, chlorinated solvents, THF, dioxanone and the like and mixtures thereof with hexane being preferred. The first solution is typically formed from Syl-Off DC 23 or MED1-4162 with hexane with Syl-Off DC 23 or MED1-4162 being present in the concentration range of from about 10 g/l to about 70 g/l and preferably from about 35 g/l to about 45 g/l.

The second solution, also under preferred conditions, can be prepared in the form of a dilute organic solution, e.g., one prepared with a solvent such as, for example, a hydrocarbon solvent possessing from about 5 to about 10 carbon atoms, e.g., pentane, hexane, heptane, octane, etc., trichlorotrifluoroethane, 1,1,1-trichloroethane, mineral spirits, alcohols, e.g., isopropyl alcohol, and the like and mixtures thereof. It is preferred to dilute MDX Fluid (or other siliconization material) with hexane and isopropyl alcohol with MDX Fluid being present in the concentration range of from about 10 g/l to about 80 g/l and preferably from about 20 g/l to about 40 g/l. In a preferred embodiment, the siliconization material is a mixture of MED1-4162 and MDX Fluid.

The mixture will ordinarily be formed by adding the first solution of the polydialkylsiloxane in solvent with the second solution of the siliconization material in solvent in a ratio ranging from about 12:1 to about 1:12, preferably from about 6:1 to about 1:6 and more preferably from about 2:1 to about 1:2. As one skilled in the art will readily appreciate, the amount of the first and second solutions necessary in forming the mixtures herein will vary depending on the volume of mixture desired.

Once the coating mixture is formed, it can then be applied to the foregoing needles employing techniques known to one skilled in the art, e.g., by dipping, wiping, spraying, total immersion, etc, with dipping and spraying being the preferred techniques. Preferably, the needles are dipped into the coating mixture for about 5 to about 60 seconds, preferably about 10 to about 45 seconds and more preferably from about 15 to 30 seconds to form a coating on the needles. After evaporation of any dilutant or solvent carrier, the siliconized coating is cured to the desired degree.

The coating can be cured by, for example, first placing the coated needle in a humid environment, e.g., a humidification chamber, and exposing the coated needle to a temperature of from about 10° C. to about 50° C. and preferably from about 20° C. to about 35° C. in a relative humidity of from about 20% to about 80% and preferably from about 50% to about 65%. The coated needles are subjected to the foregoing temperatures and humidities to initiate curing to the desired degree and provide an improved lubrication coating. Typically, a time period ranging from about 1 hour to about 6 hours and preferably from about 2 hours to about 4 hours is employed. The coated needles are then placed in, e.g., furnace or oven, and cured by heating the needles to a temperature of from about 100° C. to about 200° C., preferably from about 110 C. to about 150° C. and more preferably from about 115° C. to about 150° C. for a time period ranging from about 2 hours to about 48 hours and preferably from about 15 hours to about 25 hours such that cross-linking of the polydialkylsiloxane and siliconization material occurs. In a particularly useful embodiment, the coated needles are heated to a temperature of 140° C. for 4 hours and a temperature of 120° C. for 20 hours.

In another embodiment of the present disclosure, the coating mixture herein is formed from at least a polydialkylsiloxane and a siliconization material which does not covalently bond with the polydialkylsiloxane. A suitable polydimethylsiloxane for use herein which does not covalently bond with the siliconization material is a product sold by NuSil Technology under the name "MED-4162". Generally, the mixture is formed by adding a first solution containing at least the polydimethylsiloxane in a solvent with the second solution discussed hereinabove. The first solution is preferably formed employing the polydimethylsiloxane MED-4162 in a solvent such as, for example, a hydrocarbon solvent having from about 5 to about 10 carbon atoms, e.g., pentane, hexane, heptane, octane, etc., xylene, and the like and mixtures thereof with hexane being preferred. It is particularly preferred to form the first solution from MED-4162 in hexane in generally the same ranges as the first solution discussed above and then adding the first solution and second solution in generally the same ratios as discussed above to form the coating mixture. Once the mixture is formed, it can then be applied to the surface of a surgical needle employing generally the same techniques and parameters as discussed above. The coating mixture is then subjected to curing conditions, e.g., the curing steps discussed above, such that the siliconization material polymerizes and cross-links thereby interlocking the polydimethylsiloxane in the coating resulting in an interpenetrating networked coating.

The following non-limiting examples are illustrative of the siliconized surgical needles and the method for their manufacture of the present disclosure.

EXAMPLES

This Example compared the lubricity of needles pretreated with acid in accordance with the present disclosure with those that were not subjected to the pretreatment step.

A first batch of needles were prepared that were not subjected to the pretreatment step. These needles were coated with Dow Corning® MDX4-4159 Fluid. The MDX Fluid was applied as a spray, and the needles were held at 25° C., in 57% relative humidity, for 4 hours, and then held at 120° C. for 44 hours. Five needles were tested by passing a needle through Porvair (Inmont Corporation), a microporous polyurethane membrane of about 0.042 inches thickness which served to simulate flesh and is known to those skilled in the art to be representative of tissue. The amount of force in grams to achieve penetration of the Porvair by the needle was then measured for each of eight successive penetrations of the 5 needles for each trial.

Measurement of the needle penetration force was accomplished using the test procedure and apparatus described in U.S. Pat. No. 5,181,416, the contents of which are incorporated by reference herein. The test was performed by a testing fixture and an Instron Universal Testing Machine. The surgical needles were mounted in a gripping clamp which fixed the needle in a position perpendicular to the Porvair surface and oriented on its radial profile with the axis of rotation on the same plane as the plane of the Porvair. The needle was rotated into the Porvair which was mounted on top of an Instron load cell. The maximum amount of vertical force is recorded as the needle is pushed through the Porvair. The results of these tests are set forth below in Table 1, with the averages of the data summarized in Table 2.

TABLE 1

| TRIAL | Needle 1 | Needle 2 | Needle 3 | Needle 4 | Needle 5 |
|---|---|---|---|---|---|
| 1 | 50.1 | 62.4 | 56.0 | 48.8 | 56.0 |
| 2 | 51.0 | 58.1 | 52.7 | 49.7 | 54.6 |
| 3 | 52.9 | 66.0 | 51.9 | 52.2 | 53.0 |
| 4 | 55.8 | 74.9 | 50.2 | 61.2 | 51.4 |
| 5 | 61.1 | 85.8 | 55.3 | 55.6 | 53.3 |
| 6 | 64.2 | 96.4 | 49.7 | 60.1 | 53.4 |
| 7 | 69.7 | 97.0 | 55.4 | 58.1 | 58.8 |
| 8 | 67.5 | 111.3 | 56.8 | 62.7 | 59.1 |

TABLE 2

| | Average of force for 5 Needles | sigma | min | max |
|---|---|---|---|---|
| | 54.66 | 5.45 | 48.8 | 62.4 |
| | 53.22 | 3.29 | 49.7 | 58.1 |
| | 55.20 | 6.06 | 51.9 | 66.0 |
| | 58.70 | 10.03 | 50.2 | 74.9 |
| | 62.22 | 13.50 | 53.3 | 85.8 |
| | 64.76 | 18.57 | 49.7 | 96.4 |
| | 67.80 | 17.21 | 55.4 | 97.0 |
| | 71.48 | 22.62 | 56.8 | 111.3 |
| overall average: | 61.0 | 13.97 | 48.8 | 111.3 |

A separate batch of needles were treated as above, except they were first subjected to a pretreatment process. According to the pretreatment process, needles were first placed into a citric acid bath, one part CitriSurf™ 2250 (Stellar Solutions, Algonquin, Ill.) with ten parts of water, to achieve a pH of between 3.5 and 4.5. The tank was filled with sufficient volume of the pretreatment solution to adequately cover all needles to be treated and the temperature of the solution was maintained at 150° C. The needles were immersed in the solution for 20 minutes.

The needles were then dipped into water at ambient temperature for 1 minute, then rinsed with water heated to 60° C. for 10 minutes, and then sprayed with hot tap water for 1 minute. After rinsing, the needles were then subjected to air heated to 90° C. for 60 minutes to allow the needles to dry.

After pretreatment, needles were coated with MDX Fluid in the same fashion described above for those needles not subjected to the pretreatment step, subjected to heating at 25° C. for 4 hours at 57% relative humidity, and then held at 120° C. for 44 hours. Penetration forces were measured for five needles as described above, with the results of eight successive penetrations of the five needles set forth below in Table 3, and the average data reported in Table 4.

TABLE 3

| TRIAL | Needle 1 | Needle 2 | Needle 3 | Needle 4 | Needle 5 |
|---|---|---|---|---|---|
| 1 | 57.4 | 62.4 | 58.1 | 61.3 | 45.1 |
| 2 | 57.7 | 56.5 | 56.9 | 56.1 | 53.0 |
| 3 | 57.7 | 55.4 | 55.3 | 56.0 | 51.3 |
| 4 | 56.9 | 54.5 | 52.7 | 53.5 | 58.1 |
| 5 | 61.3 | 54.2 | 53.3 | 52.7 | 63.1 |
| 6 | 67.2 | 54.4 | 52.5 | 57.7 | 71.1 |
| 7 | 67.9 | 52.9 | 52.9 | 61.9 | 64.7 |
| 8 | 60.7 | 54.1 | 53.9 | 59.1 | 68.0 |

TABLE 4

| | Average of force for 5 Needles | sigma | min | max |
|---|---|---|---|---|
| | 56.86 | 6.90 | 45.1 | 62.4 |
| | 56.04 | 1.80 | 53.0 | 57.7 |
| | 55.14 | 2.35 | 51.3 | 57.7 |
| | 55.14 | 2.29 | 52.7 | 58.1 |
| | 56.92 | 4.89 | 52.7 | 63.1 |
| | 60.58 | 8.16 | 52.5 | 71.1 |
| | 60.06 | 6.87 | 52.9 | 67.9 |
| | 59.16 | 5.78 | 53.9 | 68.0 |
| overall average: | 57.5 | 5.30 | 45.1 | 71.1 |

As can be seen by a comparison of Tables 3 and 4 with Tables 1 and 2, needles subjected to the pretreatment solution had improved lubricity and reduced penetration forces.

It will be understood that various modifications may be made to the embodiments disclosed herein. Therefore the above description should not be construed as limiting, but merely as exemplifications of preferred embodiments. For example, metal surfaces other than needles can be coated with the coating mixture in accordance with the methods described herein. Those skilled in the art will envision other modifications within the scope and spirit of the claims appended hereto.

What is claimed is:

1. A surgical needle having reduced penetration force comprising:

a surgical needle having an acid-treated surface; and a silicone-containing coating on at least a portion of the acid treated surface, wherein the surgical needle has a penetration force on a fifth pass through tissue that is at least 10% less than the penetration force on a fifth pass through tissue of a needle having the same silicone-containing coating on the same surgical needle having no surface that is acid treated.

2. A surgical needle as in claim 1 wherein the silicone-containing coating comprises an aminoalkyl siloxane.

3. An article of manufacture as in claim 1 wherein the silicone-containing coating comprises an interpenetrating network.

4. An article of manufacture as in claim 1 wherein the silicone-containing coating comprises a copolymer of an aminoalkyl siloxane and a second siliconization material.

* * * * *